US009895402B2

(12) United States Patent
Kwack et al.

(10) Patent No.: US 9,895,402 B2
(45) Date of Patent: Feb. 20, 2018

(54) *LACTOBACILLUS PLANTARUM* **ISOLATED FROM LEAVES OF *CAMELLIA SINENSIS***

(71) Applicant: AMOREPACIFIC CORPORATION, Seoul (KR)

(72) Inventors: Il Young Kwack, Yongin-si (KR); Se Jin You, Yongin-si (KR); Tae Hun Park, Yongin-si (KR); Bum Jin Lee, Yongin-si (KR); Kye Ho Shin, Yongin-si (KR); Jin Oh Chung, Yongin-si (KR); Jun Cheol Cho, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/097,877

(22) Filed: Apr. 13, 2016

(65) Prior Publication Data

US 2016/0228480 A1    Aug. 11, 2016

Related U.S. Application Data

(60) Continuation of application No. 14/670,121, filed on Mar. 26, 2015, now abandoned, which is a division of application No. 14/124,483, filed as application No. PCT/KR2012/004569 on Jun. 8, 2012, now abandoned.

(30) Foreign Application Priority Data

Jun. 10, 2011 (KR) .................. 10-2011-0056465
Jun. 10, 2011 (KR) .................. 10-2011-0056466
Jun. 10, 2011 (KR) .................. 10-2011-0056468
Jun. 10, 2011 (KR) .................. 10-2011-0056469

(51) Int. Cl.

| *A61K 35/747* | (2015.01) |
| *C12R 1/25* | (2006.01) |
| *C12N 1/20* | (2006.01) |
| *A23L 29/00* | (2016.01) |
| *C12P 7/56* | (2006.01) |
| *A61K 36/82* | (2006.01) |
| *A61K 35/00* | (2006.01) |

(52) U.S. Cl.
CPC .......... *A61K 35/747* (2013.01); *A23L 29/065* (2016.08); *C12N 1/20* (2013.01); *C12R 1/25* (2013.01); *A23Y 2220/67* (2013.01); *A61K 36/82* (2013.01); *A61K 2035/115* (2013.01); *C12P 7/56* (2013.01)

(58) Field of Classification Search
None
See application file for complete search history.

(56) References Cited

U.S. PATENT DOCUMENTS

| 5,049,440 | A | 9/1991 | Bornhoeft, III et al. |
| 2005/0196480 | A1 | 9/2005 | Sullivan et al. |
| 2010/0034907 | A1 | 2/2010 | Daigle et al. |

FOREIGN PATENT DOCUMENTS

| JP | 2002330725 | | 11/2002 | |
| JP | 2003513649 | | 4/2003 | |
| KR | 1020060005356 | A | 1/2006 | |
| KR | 1020080102773 | A | 11/2008 | |
| KR | 20090040025 | A * | 4/2009 | |
| KR | 100909452 | B1 | 7/2009 | |
| KR | 100911115 | B1 | 8/2009 | |
| KR | 100973977 | B1 | 8/2010 | |
| KR | 1020100099536 | A | 9/2010 | |
| WO | 01034168 | A1 | 5/2001 | |
| WO | WO 2011092261 | A1 * | 8/2011 | ............. A61K 35/74 |

OTHER PUBLICATIONS

Derwent English abstract for KR 2009040025. Published Apr. 23, 2009.*
English translation of KR 2009040025. Published Apr. 23, 2009. (Year: 2009).*
Chinese Office Action—Chinese Application No. 201280038929.2 dated Aug. 25, 2015, citing the reference listed above.
Curk, M. et al., *Lactobacillus paraplantarum* sp. nov., a new species related to *Lactobacillus plantarum*. International Journal of Systematic Bacteriology, 1996, vol. 46, No. 2, pp. 429-434.
Final OA, dated Jan. 13, 2016, U.S. Appl. No. 14/670,121.
Final OA, dated Jan. 14, 2016, U.S. Appl. No. 14/670,068.
Final OA, dated Jan. 14, 2016, U.S. Appl. No. 14/670,099.
FOA, dated Oct. 6, 2015, U.S. Appl. No. 14/124,483.
Gharaei-Fathabad, E et al., Isolation and applications of one strain of *Lactobacillus paraplantarum* from tea leaves (*Camellia sinensis*). American Journal of Food Technology, May 2011, vol. 6, No. 5, pp. 429-434.
International Search Report with English Translation for International Application No. PCT/KR2012/004569 dated Dec. 26, 2012.
Lai Wen, et al., "Identification ofa cholesterol reducing lactic acid bacteria and its tolerance in在 v/mo gastroenteric environment", China Brewing, No. 3, Serial No. 228, p. 90-93, (2011).
Myung-Hee Lee, et al., "Quality and antioxidant activity of ginseng seed processed by fermentation strains", J. Ginseng Res. 39 (2015) 178-182.
NFOA, dated Jul. 8, 2015, U.S. Appl. No. 14/670,068.
NFOA, dated Jul. 8, 2015, U.S. Appl. No. 14/670,121.
Non-Final Office Action, dated Apr. 1, 2015, U.S. Appl. No. 14/124,483.
Soundharrajan Ilavenil, et al., "Probiotic Potential of *Lactobacillus* Strains with Antifungal Activity Isolated from Animal Manure", The Scientific World Journal, vol. 2015, 10 pp.
Torriani, S. et al., Differentiation of *Lactobacillus plantarum*, L. *pentosus*, and L. *paraplantarum* by recA gene sequence analysis and multiplex PCR assay with recA gene-derived primers, Applied and Microbiology, 2001, vol. 67, No. 3, pp. 3450-3454.

(Continued)

*Primary Examiner* — Renee Claytor
*Assistant Examiner* — Susan E. Fernandez
(74) *Attorney, Agent, or Firm* — Cantor Colburn LLP

(57) ABSTRACT

Disclosed are novel *Lactobacillus plantarum* strains as well as a composition containing the novel *Lactobacillus plantarum* strains or a culture thereof.

6 Claims, No Drawings

(56) References Cited

OTHER PUBLICATIONS

Written Opinion for International Application No. PCT/KR2012/004569 dated Dec. 26, 2012.
D.H. Tambekar, et al., "Acid and Bile Tolerance, Antibacterial Activity, Antibiotic Resistance and Bacteriocins Activity of Probiotic *Lactobacillus* Species", Recent Research in Science and Technology 2010, 2(4):94-98.
Korean Office Action dated Nov. 9, 2016, corresponding to Application No. KR 10-2011-0056468.
Japanese Office Action dated Mar. 15, 2016, for application No. JP 2014-514809, with English translation including a statement of relevance for the reference Nippon Nogeikagaku Kaishi vol. 33 (1959) No. 7, pp. 623-626.
Chinese Office Action dated Jun. 12, 2017, in corresponding patent application No. 201280038929.2.
Hui Zhao, "Construction and application of engineered *Lactobacillus plantarum* which yields high L-lactic acids", Heilongjiang University Publisher; edition No. 1, 2010. Partial translation.

\* cited by examiner

LACTOBACILLUS PLANTARUM ISOLATED FROM LEAVES OF CAMELLIA SINENSIS

CROSS-REFERENCE TO RELATED APPLICATION

This application is continuation of U.S. patent application Ser. No. 14/670,121, filed on Mar. 26, 2015, which is a divisional of U.S. patent application Ser. No. 14/124,483, filed on Dec. 6, 2013, which claims priority to PCT Application No. PCT/KR2012/004569, filed on Jun. 8, 2012, which claims priority to Korean Patent Application No. 10-2011-0056465, filed on Jun. 10, 2011, Korean Patent Application No. 10-2011-0056466, filed on Jun. 10, 2011, Korean Patent Application No. 10-2011-0056468, filed on Jun. 10, 2011, and Korean Patent Application No. 10-2011-0056469, filed on Jun. 10, 2011, and all the benefits accruing therefrom under 35 U.S.C. §119, the contents of which in its entirety are herein incorporated by reference.

TECHNICAL FIELD

The present disclosure relates to a novel *Lactobacillus plantarum* isolated from tea tree (*Camellia sinensis*) leaves.

BACKGROUND ART

Tea for drinking is one obtained by deactivating oxygenase present in shoots or leaves of theaceous *Camellia sinensis* and removing water therefrom. It contains caffeine, tannin, flavonoids, essential oils and the like as well as vitamins, and has been widely used at various fields such as a food field.

DISCLOSURE

Technical Problem

The present disclosure is directed to providing a novel *Lactobacillus plantarum* strain. Further, it is directed to providing a composition including the novel *Lactobacillus plantarum* strain or a culture solution thereof.

Technical Solution

In one aspect, there is provided a *Lactobacillus plantarum* APsulloc 331261 strain.

In one aspect, there is provided a *Lactobacillus plantarum* APsulloc 331263 strain.

In one aspect, there is provided a *Lactobacillus plantarum* APsulloc 331266 strain.

In one aspect, there is provided a *Lactobacillus plantarum* APsulloc 331269 strain.

In another aspect, there is provided a composition including at least one of the *Lactobacillus plantarum* APsulloc 331261 strain, the APsulloc 331263 strain, the APsulloc 331266 strain and the APsulloc 331269 strain, or a culture solution thereof.

Advantageous Effects

The novel *Lactobacillus plantarum* strain according to the present disclosure is excellent in acid resistance, and therefore, it is also viable in the stomach when it is taken by a food, and further, it may have higher intestinal deliverity. The *Lactobacillus plantarum* strain according to the present disclosure is excellent in bile acid resistance, and therefore, it is superior to intestinal fix. Further, the *Lactobacillus plantarum* strain according to the present disclosure is excellent in antibacterial activity, and therefore, it is superior to harmful bacteria inhibitory effect. The *Lactobacillus plantarum* strain according to the present disclosure has lower D-lactic acid ratio in the produced lactic acid than the existing *Lactobacillus plantarum*. Accordingly, even adults or infants, who are susceptible to lactic acid, may freely intake the strain. The *Lactobacillus plantarum* strain according to the present disclosure produces fewer amount of lactic acid than the existing *Lactobacillus plantarum*, and therefore, when foods are fermented by using thereof, the foods may have gentle flavor. Thus, the novel *Lactobacillus plantarum* strain according to the present disclosure may be widely used in various fields, for example, a food field.

BEST MODE

Lactic acid bacteria are bacteria producing lactic acid by degrading sugar such as glucose. The lactic acid produced by lactic acid fermentation of lactic acid bacteria may prevent growth of pathogens and harmful bacteria, and this characteristic is used for producing foods such as dairy foods, kimchis, brewed foods and the like. Further, the lactic acid bacteria live in the intestine of mammals and inhibit abnormal fermentation by various germs, and therefore, those are important bacteria useful as a medicine for intestinal disorders.

*Lactobacillus plantarum* is a strain belongs to the lactic acid bacteria, and it is known to mainly grow when kimchi is much fermented and tastes sour. Optical isomers of the produced lactic acid are D-type and L-type. The *Lactobacillus plantarum* may be widely used to various foods need fermentation. Accordingly, if a *Lactobacillus plantarum* having excellent acid resistance, bile acid resistance and antibacterial activity is developed, it may be usefully used.

Hereinafter, the present disclosure now will be described in detail.

One aspect of the present disclosure provides a *Lactobacillus plantarum* APsulloc 331261 (Accession No.: KCCM11179P) strain. One aspect of the present disclosure provides a *Lactobacillus plantarum* APsulloc 331263 (Accession No.: KCCM11180P) strain. One aspect of the present disclosure provides a *Lactobacillus plantarum* APsulloc 331266 (Accession No.: KCCM11181P) strain. One aspect of the present disclosure provides a *Lactobacillus plantarum* APsulloc 331269 (Accession No.: KCCM11182P) strain.

At least one of the *Lactobacillus plantarum* APsulloc 331261, the APsulloc 331263, the APsulloc 331266 and the APsulloc 331269 according to the present disclosure is a strain isolated from tea tree (*Camellia sinensis*) leaves, and belongs to *Lactobacillus plantarum*. Specifically, the *Lactobacillus plantarum* strain according to the present disclosure may be isolated by a method containing: a step of salting the tea tree leaves in salt of 5 to 15 wt %, based on the weight of the tea tree leaves; a step of mixing the salted tea tree leaves with a sugar solution, for example, 0.1% to 3% fructooligosaccharide, followed by culturing at 25 to 35° C. for 1 to 5 days; and a step of collecting the solution cultured to less than pH 5, followed by culturing at anaerobic condition of 25 to 35° C. for 1 to 5 days.

At least one of the *Lactobacillus plantarum* APsulloc 331261, the APsulloc 331263, the APsulloc 331266 and the APsulloc 331269 according to one aspect of the present disclosure has excellent acid resistance. When intaking lactic acid bacteria, for example, *Lactobacillus plantarum* as a probiotic, it is preferred to have higher intestinal deliverity, in order to display characteristic effects of the lactic acid bacteria. In order to enhance the intestinal deliverity, viability in the stomach, where pH is low due to gastric acid secretion, should be high. It is known that pH of the empty stomach may be about 1.2 to 2, but when taking foods, pH may be about 2 to 3. The *Lactobacillus plantarum* strain according to the present disclosure may have excellent acid resistance at more than pH 2 to 4, specifically more than pH 2 to 3.5 or pH 2.5 to 4, more specifically pH 2.5 to 3.5, further more specifically about pH 2.5 to 3. On the other hand, when intaking foods, it is known that the average retention time of the foods may be about 1 to 3 hours. The *Lactobacillus plantarum* strain according to the present disclosure may have excellent acid resistance for 0.5 to 5 hours, specifically for 1 to 4 hours, at more than pH 2 to pH 4, specifically more than pH 2 to pH 3.5 or pH 2.5 to 4, more specifically pH 2.5 to 3.5, further more specifically pH 2.5 to 3. Thus, the *Lactobacillus plantarum* strain according to the present disclosure, which is viable even at lower pH of the stomach during the time stayed in the stomach, may have high intestinal deliverity when it is taken as a food.

The *Lactobacillus plantarum* strain according to one aspect of the present disclosure has excellent bile acid resistance. The foods passed through the stomach are delivered into the intestine, and at this time, the secreted bile acid helps food digestion. It is known that the strain having high bile acid resistance has good intestinal fix. The *Lactobacillus plantarum* strain according to one aspect of the present disclosure having excellent bile acid resistance is superior to the intestinal fix.

The *Lactobacillus plantarum* strain according to one aspect of the present disclosure has lactic acid producing ability. In general, the lactic acid produced by lactic acid bacteria may be L-type and D-type. Of them, the metabolic rate of the D-lactic acid in the body is lower than the L-lactic acid. Accordingly, the higher blood D-lactic acid concentration may cause lactic acid toxicosis. Thus, it is preferred that adults or infants, who are susceptible to lactic acid, do not take lactic acid bacteria, which largely produces D-lactic acid, if possible.

The *Lactobacillus plantarum* strain according to another aspect of the present disclosure may produce lactic acid containing D-type in an amount of 75% or less, specifically 70% or less, more specifically 65% or less.

The *Lactobacillus plantarum* strain according to further another aspect of the present disclosure may produce lactic acid in an amount of 17.5 g/L or less, specifically 17 g/L or less, more specifically 16.5 g/L or less, further more specifically 15 g/L or less, further more specifically 14.5 g/L or less, further more specifically 14 g/L or less, further more specifically 13.5 g/L or less.

Like this, because the *Lactobacillus plantarum* strain according to the present disclosure produces lactic acid containing D-type with lower rate than the existing *Lactobacillus plantarum*, adults or infants, who are susceptible to lactic acid, may freely take it. Further, because its lactic acid yield is lower than the existing *Lactobacillus plantarum*, when fermenting foods by using thereof, the foods may have gentler flavor.

One aspect of the present disclosure provides an extract or a culture solution of at least one of the *Lactobacillus plantarum* APsulloc 331261 strain, the APsulloc 331263 strain, the APsulloc 331266 strain and the APsulloc 331269 strain. Another aspect of the present disclosure provides a composition containing at least one of the *Lactobacillus plantarum* APsulloc 331261 strain, the APsulloc 331263 strain, the APsulloc 331266 strain and the APsulloc 331269 strain, an extract thereof, or a culture solution thereof.

One aspect of the present disclosure provides a food composition containing at least one selected from the *Lactobacillus plantarum* APsulloc 331261 strain, the APsulloc 331263 strain, the APsulloc 331266 strain and the APsulloc 331269 strain, its extract, or its culture solution.

The food composition may be a health food composition, and also may be a fermented food composition, which needs fermentation, for example, teas, dairy goods, kimchis, brewed foods.

The formulation of the food composition is not particularly limited, but for example, it may be formulated into tablet, pill, hard or soft capsule, granule, drink, caramel, diet bar, tea bag and the like. The health food composition may further comprise, in addition to the active ingredient, commonly used other ingredients, which may be suitably selected by those skilled in the art depending on the formulation or purpose of the composition. The addition of the other ingredients may give a synergic effect.

Determination of the dose of the active ingredient is within the level of those skilled in the art. For example, its daily dose may be *Lactobacillus plantarum* about $10^5$ to $10^{13}$ CFU/day, more specifically about $10^6$ to $10^{10}$ CFU/day, but is not limited thereto, and may be varied with various factors including the age, physical condition, complication, etc. of a subject to be treated.

One aspect of the present disclosure provides a cosmetic composition containing at least one of the *Lactobacillus plantarum* APsulloc 331261 strain, the APsulloc 331263 strain, the APsulloc 331266 strain and the APsulloc 331269 strain, an extract thereof, or a culture solution thereof. The cosmetic composition may be provided as any formulation suitable for topical application. For example, it may be provided as a formulation of oil in water emulsion, water in oil emulation, suspension, solid, gel, powder, paste, foam or aerosol composition. The composition of the said formulation may prepared by a conventional method in the art.

The cosmetic composition may further include other ingredients, which may not adversely affect a main desired effect, preferably may provide a synergic effect to the main effect. The cosmetic composition according to the present disclosure may include a material selected from the group consisting of vitamin, polymer peptide, polysaccharide and spingolipid. Further, the cosmetic composition according to the present disclosure may include moisturizing agent, emollient, surfactant, UV absorbing agent, preservative, disinfecting agent, antioxidant, pH modifier, organic and inorganic dye, aromatic, cooling agent or antiperspirant. The amount of the ingredients may be suitable selected in such a manner that they may not adversely affect the purpose and effect of the present disclosure, and the amount may be 0.01 to 5 wt %, specifically 0.01 to 3 wt %, based on the total weight of the composition.

One aspect of the present disclosure provides a pharmaceutical composition containing at least one of the *Lactobacillus plantarum* APsulloc 331261 strain, the APsulloc 331263 strain, the APsulloc 331266 strain and the APsulloc 331269 strain, an extract thereof, or a culture solution thereof. The pharmaceutical composition may be used for preventing or treating intestinal disorder such as irritable bowel syndrome, constipation and diarrhea.

The pharmaceutical composition according to one aspect of the present disclosure may be administered orally or parenterally, e.g., rectally, topically, transdermally, intravenously, intramuscularly, intra-abdominally, subcutaneously, etc. Examples of formulations for oral administration include tablet, pill, soft or hard capsule, granule, powder, fine granule, solution, emulsion, pellet and the like, but not limited thereto. Examples for formulations for parenteral administration include solution, suspension, lotion, gel, injectable solution, drop, suppository, patch or spray, but not limited thereto. The formulation may be easily formulated according to conventional methods, and surfactants, excipients, wetting agent, emulsifier, suspending agent, salt or buffer for osmotic pressure control, colorant, flavoring agent, stabilizer, preservative, preserved agent or other conventional additives may be suitably used for the formulation.

Active ingredient of the pharmaceutical composition according to one aspect of the present disclosure may be varied with the age, sex and body weight of a subject to be treated, pathological condition be treated, severity of the pathological condition, administration route and the judgment of a prescriber. Determination of the dose considering these factors is within the level of those skilled in the art. For example, the daily dose may be 0.1 mg/kg/day to 5000 mg/kg/day, specifically 50 mg/kg/day to 500 mg/kg/day, but not limited thereto.

The *Lactobacillus plantarum* APsulloc 331261, the APsulloc 331263, the APsulloc 331266 and the APsulloc 331269 are deposited at Korean Culture Center of Microorganisms (KCCM, address: 361-221, Yurim B/D. hongje-1-dong, Seodaemun-gu, Seoul, Republic of Korea) on Mar. 28, 2011 under Accession Nos.: KCCM11179P, KCCM11180P, KCCM11181P and KCCM11182P.

(1) *Lactobacillus plantarum* APsulloc 331261
Depository Institution Name: Korean Culture Center of Microorganisms
Accession No.: KCCM11179P
Deposition Date: 2011 Mar. 28
(2) *Lactobacillus plantarum* APsulloc 331263
Depository Institution Name: Korean Culture Center of Microorganisms
Accession No.: KCCM11180P
Deposition Date: 2011 Mar. 28
(3) *Lactobacillus plantarum* APsulloc 331266
Depository Institution Name: Korean Culture Center of Microorganisms
Accession No.: KCCM11181P
Deposition Date: 2011 Mar. 28
(4) *Lactobacillus plantarum* APsulloc 331269
Depository Institution Name: Korean Culture Center of Microorganisms
Accession No.: KCCM11182P
Deposition Date: 2011 Mar. 28

Hereinafter, isolation methods, identification methods and characteristics of the novel *Lactobacillus plantarum* strains according to the present disclosure now will be described in detail with reference to the examples (and experiments). However, the following examples (and experiments) are for illustrative purposes only and not intended to limit the scope of this disclosure.

[Example 1] Isolation of *Lactobacillus Plantarum* Strain

Tea tree leaves 200 g are washed twice with distilled water to remove impurities. Moisture is cleared off from the washed tea tree leaves. Then, the tea tree leaves are mixed with table salt of 8 wt %, based on the weight of the tea tree leaves, and then stored at room temperature for 3 hours. The salted tea tree leaves are mixed with 1% fructooligosaccharide solution 1000 mL, and then incubated in an incubator at 32° C. for 3 days. 3 days later, whether pH of the cultured solution is lowered to less than 5 is checked, and in the case of less than pH 5, the cultured solution is collected and incubated in Difco Lactobacilli MRS Agar® medium. At this time, the incubation is conducted in a 32° C., anaerobic chamber for 2 days, and then white colonies are collected.

Through the method described above, *Lactobacillus plantarum* APsulloc 331261, APsulloc 331263, APsulloc 331266 and APsulloc 331269 are isolated from tea tree leaves, respectively.

[Example 2] Identification of *Lactobacillus Plantarum* Strain (1) Strain Culture
The APsulloc 331261 isolated in Example 1 is streaked on a MRS agar plate, and cultured at 37° C. for 2 days. The obtained single colony is inoculated to MRS broth 10 mL, and then cultured at 37° C. overnight to prepare a *Lactobacillus plantarum* strain culture solution. The method described above is repeated to the APsulloc 331263, the APsulloc 331266 and the APsulloc 331269, respectively, to prepare *Lactobacillus plantarum* strain culture solutions.
(2) Analysis of Sugar Fermentation Pattern of *Lactobacillus Plantarum* Strain
The APsulloc 331261 strain culture solution prepared as described in (1) is inoculated to MRS broth 10 mL to the concentration of 0.5% and cultured at 37° C. overnight. The culture solution is centrifuged at 8,000 rpm for 5 min, supernatant is removed, and then only bacteria are collected. Then, 0.85% saline buffer 2 mL is added to the bacteria and suspended. Later process is conducted by using API 50CHL kit (Biomerieux) according to a manufacturer's protocol. Specific process is as follows.

First of all, while gradually adding the strain suspension to API suspension medium 5 mL, the amount of suspension needed to make cloudiness of about McFarland Standard 2 (Biomerieux) is measured. Twice of the measured amount of the suspension is added to API 50CHL medium 10 mL, and then shaken for mixing. The above mixture is added to cupules containing different substrate, one drop of mineral oil is put thereto, and then the mixture is cultured at 37° C. for 2 days to analyze sugar fermentation pattern.

The method described above is repeated to culture solutions of the APsulloc 331263, the APsulloc 331266 and the APsulloc 331269 strain to analyze sugar fermentation pattern.

The results of sugar fermentation patterns of the APsulloc 331261, the APsulloc 331263, the APsulloc 331266 and the APsulloc 331269, compared with *Lactobacillus plantarum* strain (KCTC3108) as a standard strain, and the results of identification of the APsulloc 331261, the APsulloc 331263, the APsulloc 331266 and the APsulloc 331269 by using the above results are as shown in the following Tables. Table 1: APsulloc 331261, Table 2: APsulloc 331263, Table 3: APsulloc 331266 and Table 4: APsulloc 331269.

TABLE 1

| Substrate | KCTC3108 | | APsulloc 331261 | |
|---|---|---|---|---|
| | 24 h | 48 h | 24 h | 48 h |
| Control | − | − | − | − |
| Glycerol | − | − | − | − |
| Erythritol | − | − | − | − |
| D-Arabinose | − | − | − | − |
| L-Arabinose | + | + | + | + |

TABLE 1-continued

| Substrate | KCTC3108 24 h | KCTC3108 48 h | APsulloc 331261 24 h | APsulloc 331261 48 h |
|---|---|---|---|---|
| Ribose | + | + | + | + |
| D-Xylose | − | − | − | − |
| L-xylose | − | − | − | − |
| Adonitol | − | − | − | − |
| β-Methyl-D-xylose | − | − | − | − |
| Galactose | + | + | + | + |
| Glucose | + | + | + | + |
| Fructose | + | + | + | + |
| Mannose | + | + | + | + |
| Sorbose | − | − | − | − |
| Rhamnose | − | − | − | − |
| Dulcitol | − | − | − | − |
| Inositol | − | − | − | − |
| Mannitol | + | + | + | + |
| Sorbitol | + | + | + | + |
| α-Methyl-D-mannoside | ? | + | − | − |
| α-Methyl-D-glucoside | − | − | − | − |
| N-Acetyl-glucosamine | + | + | + | + |
| Amygdalin | + | + | + | + |
| Arbutin | + | + | + | + |
| Esculin | + | + | + | + |
| Salicin | + | + | + | + |
| Cellobiose | ? | + | + | + |
| Maltose | + | + | + | + |
| Lactose | + | + | + | + |
| Melibiose | + | + | + | + |
| D-Saccharose (Sucrose) | + | + | + | + |
| Trehalose | + | + | + | + |
| Inulin | − | − | − | − |
| Melezitose | + | + | + | + |
| Raffinose | − | − | + | + |
| Amidon (Starch) | − | − | − | − |
| Glycogen | − | − | − | − |
| Xylitol | − | − | − | − |
| Gentiobiose | − | − | + | + |
| D-Turanose | + | + | + | + |
| D-Lyxose | − | − | − | − |
| D-Tagatose | − | − | − | − |
| D-Fucose | − | − | − | − |
| L-Fucose | − | − | − | − |
| D-Arabitol | ? | − | ? | − |
| L-Arabitol | − | − | − | − |
| Gluconic acid | ? | + | ? | + |
| 2-Ketogluconate | + | − | − | − |
| 5-Ketogluconate | − | − | − | − |

TABLE 2

| Substrate | KCTC3108 24 h | KCTC3108 48 h | APsulloc 331263 24 h | APsulloc 331263 48 h |
|---|---|---|---|---|
| Control | − | − | − | − |
| Glycerol | − | − | − | − |
| Erythritol | − | − | − | − |
| D-Arabinose | − | − | − | − |
| L-Arabinose | + | + | + | + |
| Ribose | + | + | + | + |
| D-Xylose | − | − | − | − |
| L-Xylose | − | − | − | − |
| Adonitol | − | − | − | − |
| β-Methyl-D-xylose | − | − | − | − |
| Galactose | + | + | + | + |
| Glucose | + | + | + | + |
| Fructose | + | + | + | + |
| Mannose | + | + | + | + |
| Sorbose | − | − | − | − |
| Rhamnose | − | − | − | − |
| Dulcitol | − | − | − | − |
| Inositol | − | − | − | − |
| Mannitol | + | + | + | + |
| Sorbitol | + | + | + | + |
| α-Methyl-D-mannoside | ? | + | − | − |
| α-Methyl-D-glucoside | − | − | − | − |
| N-Acetyl-glucosamine | + | + | + | + |
| Amygdalin | + | + | + | + |
| Arbutin | + | + | + | + |
| Esculin | + | + | + | + |
| Salicin | + | + | + | + |
| Cellobiose | ? | + | + | + |
| Maltose | + | + | + | + |
| Lactose | + | + | + | + |
| Melibiose | + | + | + | + |
| D-Saccharose (Sucrose) | + | + | + | + |
| Trehalose | + | + | + | + |
| Inulin | − | − | − | − |
| Melezitose | + | + | + | + |
| Raffinose | − | − | ? | + |
| Amidon (Starch) | − | − | − | − |
| Glycogen | − | − | − | − |
| Xylitol | − | − | − | − |
| Gentiobiose | − | − | + | + |
| D-Turanose | + | + | − | − |
| D-Lyxose | − | − | − | − |
| D-Tagatose | − | − | − | − |
| D-Fucose | − | − | − | − |
| L-Fucose | − | − | − | − |
| D-Arabitol | ? | − | − | − |
| L-Arabitol | − | − | − | − |
| Gluconic acid | ? | + | + | + |
| 2-Ketogluconate | − | − | − | − |
| 5-Ketogluconate | − | − | − | − |

TABLE 3

| Substrate | KCTC3108 24 h | KCTC3108 48 h | APsulloc 331266 24 h | APsulloc 331266 48 h |
|---|---|---|---|---|
| Control | − | − | − | − |
| Glycerol | − | − | − | − |
| Erythritol | − | − | − | − |
| D-Arabinose | − | − | − | − |
| L-Arabinose | + | + | + | + |
| Ribose | + | + | + | + |
| D-Xylose | − | − | − | − |
| L-Xylose | − | − | − | − |
| Adonitol | − | − | − | − |
| β-Methyl-D-xylose | − | − | − | − |
| Galactose | + | + | + | + |
| Glucose | + | + | + | + |
| Fructose | + | + | + | + |
| Mannose | + | + | + | + |
| Sorbose | − | − | − | − |
| Rhamnose | − | − | − | − |
| Dulcitol | − | − | − | − |
| Inositol | − | − | − | − |
| Mannitol | + | + | + | + |
| Sorbitol | + | + | + | + |
| α-Methyl-D- | ? | + | − | − |

TABLE 3-continued

| | KCTC3108 | | APsulloc 331266 | |
|---|---|---|---|---|
| Substrate | 24 h | 48 h | 24 h | 48 h |
| Mannoside | | | | |
| α-Methyl-D-glucoside | − | − | − | − |
| N-Acetyl-glucosamine | + | + | + | + |
| Amygdalin | + | + | + | + |
| Arbutin | + | + | + | + |
| Esculin | + | + | + | + |
| Salicin | + | + | + | + |
| Cellobiose | ? | + | + | + |
| Maltose | + | + | + | + |
| Lactose | + | + | + | + |
| Melibiose | + | + | + | + |
| D-Saccharose (Sucrose) | + | + | + | + |
| Trehalose | + | + | + | + |
| Inulin | − | − | − | − |
| Melezitose | + | + | + | + |
| Raffinose | − | − | + | + |
| Amidon (Starch) | − | − | − | − |
| Glycogen | − | − | − | − |
| Xylitol | − | − | − | − |
| Gentiobiose | − | − | + | + |
| D-Turanose | + | + | + | + |
| D-Lyxose | − | − | − | − |
| D-Tagatose | − | − | − | − |
| D-Fucose | − | − | − | − |
| L-Fucose | − | − | − | − |
| D-Arabitol | ? | − | − | − |
| L-Arabitol | − | − | − | − |
| Gluconic acid | ? | + | + | + |
| 2-Ketogluconate | − | − | − | − |
| 5-Ketogluconate | − | − | − | − |

TABLE 4

| | KCTC3108 | | APsulloc 331269 | |
|---|---|---|---|---|
| Substrate | 24 h | 48 h | 24 h | 48 h |
| Control | − | − | − | − |
| Glycerol | − | − | − | − |
| Erythritol | − | − | − | − |
| D-Arabinose | − | − | − | − |
| L-Arabinose | + | + | − | − |
| Ribose | + | + | + | + |
| D-Xylose | − | − | + | + |
| L-Xylose | − | − | − | − |
| Adonitol | − | − | − | − |
| β-Methyl-D-xylose | − | − | − | − |
| Galactose | + | + | + | + |
| Glucose | + | + | + | + |
| Fructose | + | + | + | + |
| Mannose | + | + | + | + |
| Sorbose | − | − | − | − |
| Rhamnose | − | − | − | − |
| Dulcitol | − | − | − | − |
| Inositol | − | − | − | − |
| Mannitol | + | + | + | + |
| Sorbitol | + | + | + | + |
| α-Methyl-D-mannoside | ? | + | ? | + |
| α-Methyl-D-glucoside | − | − | − | − |
| N-Acetyl-glucosamine | + | + | + | + |
| Amygdalin | + | + | + | + |
| Arbutin | + | + | + | + |
| Esculin | + | + | + | + |
| Salicin | + | + | + | + |
| Cellobiose | ? | + | + | + |
| Maltose | + | + | + | + |
| Lactose | + | + | + | + |
| Melibiose | + | + | + | + |
| D-Saccharose (Sucrose) | + | + | + | + |
| Trehalose | + | + | + | + |
| Inulin | − | − | − | − |
| Melezitose | + | + | + | + |
| Raffinose | − | − | + | + |
| Amidon (Starch) | − | − | − | − |
| Glycogen | − | − | − | − |
| Xylitol | − | − | − | − |
| Gentiobiose | − | − | + | + |
| D-Turanose | + | + | + | + |
| D-Lyxose | − | − | − | − |
| D-Tagatose | − | − | − | − |
| D-Fucose | − | − | − | − |
| L-Fucose | − | − | − | − |
| D-Arabitol | ? | − | − | − |
| L-Arabitol | − | − | − | − |
| Gluconic acid | ? | + | ? | + |
| 2-Ketogluconate | − | − | − | − |
| 5-Ketogluconate | − | − | − | − |

+: Substrate is degraded,
−: Substrate is not degraded,
?: Unable to determine

TABLE 5

| Strain | Name | % Index | T Index |
|---|---|---|---|
| KCTC3108 | Lactobacillus plantarum | 99.9 | 0.8 |
| | Lactobacillus pentosus | 0.1 | 0.29 |
| APsulloc 331261 | Lactobacillus plantarum | 99.4 | 0.99 |
| | Lactobacillus pentosus | 0.4 | 0.71 |
| APsulloc 331263 | Lactobacillus plantarum | 98.9 | 0.97 |
| | Lactobacillus pentosus | 0.7 | 0.71 |
| APsulloc 331266 | Lactobacillus plantarum | 99.4 | 0.99 |
| | Lactobacillus pentosus | 0.4 | 0.71 |
| APsulloc 331269 | Lactobacillus plantarum | 99.4 | 0.79 |
| | Lactobacillus pentosus | 0.5 | 0.51 |

As can be seen from the above, all of the APsulloc 331261, the APsulloc 331263, the APsulloc 331266 and the APsulloc 331269 show the consistency (% index) to the *Lactobacillus plantarum* of 99% or more. Accordingly, it is confirmed that those strains are belong to the *Lactobacillus plantarum*.

Further, compared with the standard strain (KCTC3108), the APsulloc 331261 is different in use of α-methyl-mannoside and raffinose, the APsulloc 331263 is different in use of α-methyl-mannoside, raffinose and D-turanose, the APsulloc 331266 is different in use of α-methyl-mannoside and raffinose, and the APsulloc 331269 is different in use of L-arabinose and raffinose. Accordingly, it is confirmed that all of them are different strains from the standard strain.

(3) Analysis of Enzyme Activity Pattern of *Lactobacillus Plantarum* Strain

The APsulloc 331261 strain culture solution prepared as described in (1) is inoculated to MRS broth 10 mL to the concentration of 0.5% and cultured at 37° C. overnight. The culture solution is centrifuged at 8,000 rpm for 5 min, supernatant is removed, and then only bacteria are collected. Then, 0.85% saline buffer 2 mL is added to the bacteria and suspended. Later process is conducted by using API ZYM kit (Biomerieux) according to a manufacturer's protocol. Specific process is as follows.

First of all, while gradually adding the strain suspension to API suspension medium 5 mL, the amount of suspension needed to make cloudiness of about McFarland Standard 2 (Biomerieux) is measured. Twice of the measured amount of the suspension is added to API 50CHL medium 10 mL, and then shaken for mixing. The above mixture 65 μl is added the each cupule, and cultured at 37° C. for 4 hours. Each one drop of ZYM A reagent and ZYM B reagent is put into each cupule, and 5 min later, scored from 0 to 5 according to the color intensity, and then the score 3 or more is decided as positive.

The method described above is repeated to the APsulloc 331263, the APsulloc 331266 and the APsulloc 331269 strain culture solution to analyze enzyme activity patter.

The results of enzyme activity patterns of the APsulloc 331261, the APsulloc 331263, the APsulloc 331266 and the APsulloc 331269, compared with *Lactobacillus plantarum* strain (KCTC3108) as a standard strain are as shown in the following Tables. Table 6: APsulloc 331261, Table 7: APsulloc 331263, Table 8: APsulloc 331266 and Table 9: APsulloc 331269.

TABLE 6

| Enzyme | KCTC3108 Score | Result | APsulloc 331261 Score | Result |
|---|---|---|---|---|
| Control | 0 | − | 0 | − |
| Alkaline phosphatase | 0 | − | 1 | − |
| Esterase | 1 | − | 2 | − |
| Esterase lipase | 1 | − | 2 | − |
| Lipase | 0 | − | 2 | − |
| Leucine arylamidase | 5 | + | 4 | + |
| Valine arylamidase | 4 | + | 4 | + |
| Cystine arylamidase | 1 | − | 2 | − |
| Trypsin | 0 | − | 0 | − |
| α-Chymotrypsin | 0 | − | 1 | − |
| Acid phosphatease | 1 | − | 3 | + |
| Naphthol-AS-BI-phosphohydrolase | 1 | − | 3 | + |
| α-Galactosidase | 1 | − | 3 | + |
| β-Galactosidase | 5 | + | 5 | + |
| β-Glucuronidase | 1 | − | 2 | − |
| β-Glucosidase | 3 | + | 5 | + |
| N-Acetyl-β-glucosaminidase | 0 | − | 4 | + |
| α-Mannosidase | 0 | − | 1 | − |
| α-Fucosidase | 0 | − | 1 | − |

TABLE 7

| Enzyme | KCTC3108 Score | Result | APsulloc 331263 Score | Result |
|---|---|---|---|---|
| Control | 0 | − | 0 | − |
| Alkaline phosphatase | 0 | − | 1 | − |
| Esterase | 1 | − | 2 | − |
| Esterase lipase | 1 | − | 2 | − |
| Lipase | 0 | − | 1 | − |
| Leucine arylamidase | 5 | + | 4 | + |
| Valine arylamidase | 4 | + | 4 | + |
| Cystine arylamidase | 1 | − | 2 | − |
| Trypsin | 0 | − | 0 | − |
| α-Chymotrypsin | 0 | − | 1 | − |
| Acid phosphatease | 1 | − | 3 | + |
| Naphthol-AS-BI-phosphohydrolase | 1 | − | 3 | + |
| α-galactosidase | 1 | − | 3 | + |
| β-galactosidase | 5 | + | 5 | + |
| β-glucuronidase | 1 | − | 2 | − |
| α-glucosidase | 3 | + | 2 | − |
| β-glucosidase | 3 | + | 5 | + |
| N-acetyl-β-glucosaminidase | 0 | − | 4 | + |
| α-Mannosidase | 0 | − | 1 | − |
| α-Fucosidase | 0 | − | 1 | − |

TABLE 8

| Enzyme | KCTC3108 Score | Result | APsulloc 331266 Score | Result |
|---|---|---|---|---|
| Control | 0 | − | 0 | − |
| Alkaline phosphatase | 0 | − | 1 | − |
| Esterase | 1 | − | 1 | − |
| Esterase lipase | 1 | − | 1 | − |
| Lipase | 0 | − | 1 | − |
| Leucine arylamidase | 5 | + | 4 | + |
| Valine arylamidase | 4 | + | 3 | + |
| Cystine arylamidase | 1 | − | 2 | − |
| Trypsin | 0 | − | 1 | − |
| α-Chymotrypsin | 0 | − | 1 | − |
| Acid phosphatease | 1 | − | 3 | + |
| Naphthol-AS-BI-phosphohydrolase | 1 | − | 3 | + |
| α-galactosidase | 1 | − | 3 | + |
| β-galactosidase | 5 | + | 5 | + |
| β-glucuronidase | 1 | − | 2 | − |
| β-glucosidase | 3 | + | 5 | + |
| N-acetyl-β-glucosaminidase | 0 | − | 4 | + |
| α-Mannosidase | 0 | − | 1 | + |
| α-Fucosidase | 0 | − | 0 | − |

TABLE 9

| Enzyme | KCTC3108 Score | Result | APsulloc 331269 Score | Result |
|---|---|---|---|---|
| Control | 0 | − | 0 | − |
| Alkaline phosphatase | 0 | − | 1 | − |
| Esterase | 1 | − | 1 | − |
| Esterase lipase | 1 | − | 1 | − |
| Lipase | 0 | − | 1 | − |
| Leucine arylamidase | 5 | + | 4 | + |
| Valine arylamidase | 4 | + | 3 | + |
| Cystine arylamidase | 1 | − | 2 | − |
| Trypsin | 0 | − | 1 | − |
| α-Chymotrypsin | 0 | − | 1 | − |
| Acid phosphatease | 1 | − | 3 | + |
| Naphthol-AS-BI-phosphohydrolase | 1 | − | 3 | + |
| α-galactosidase | 1 | − | 3 | + |
| β-galactosidase | 5 | + | 5 | + |
| β-glucuronidase | 1 | − | 2 | − |
| β-glucosidase | 3 | + | 5 | + |
| N-acetyl-β-glucosaminidase | 0 | − | 4 | + |
| α-Mannosidase | 0 | − | 1 | − |
| α-Fucosidase | 0 | − | 0 | − |

As can be seen from the above, all of the APsulloc 331261, the APsulloc 331263, the APsulloc 331266 and the APsulloc 331269 have different enzyme activity intensities of acid phosphatease, naphthol-AS-BI-phosphohydrolase, α-galactosidase and N-acetyl-β-glucosaminidase from the standard strain (KCTC3108). Accordingly, it is confirmed that all of the APsulloc 331261, the APsulloc 331263, the APsulloc 331266 and the APsulloc 331269 are different strains from the standard strain.

Further, the APsulloc 331261, the APsulloc 331263, the APsulloc 331266 and the APsulloc 331269 are decided as negative against the β-glucuronidase activity known as one of representative oncogenic enzymes, which can induce cancer by modifying procarcinogen to carcinogen in the intestine. In addition, the APsulloc 331263 inhibits the α-glucosidase activity. Accordingly, it is confirmed that all of the APsulloc 331261, the APsulloc 331263, the APsulloc 331266 and the APsulloc 331269 are acceptable to be used to a food composition.

(4) Evaluation of Antibiotic Resistance of *Lactobacillus Plantarum* Strain

Sterilized MRS agar 20 mL is added to a petri dish (Diameter: 100 mm), and cooled in a clean bench to prepare a medium. The APsulloc 331261 strain culture solution prepared in (1) is inoculated to MRS broth 10 mL to the concentration of 0.5%, and then cultured at 37° C. for 6 hours. The resulting solution is diluted to have absorbance of about 0.08 to 0.13 at 625 nm. A sterilized cotton swab is fully soaked in the diluted solution, and then streaked evenly on the prepared MRS agar plate overall. An antibiotic sensitivity disk is dropped on the plate with a proper distance. After culturing at 37° C. for 24 hours, diameter of a clear zone is measured.

The method described above is repeated to the APsulloc 331263, the APsulloc 331266 and the APsulloc 331269 strain culture solutions to evaluate antibiotic resistance.

Concentration of the antibiotic sensitivity disk and evaluation standard are as follows.

TABLE 10

| Antibiotics | | Zone Diameter Analysis | | |
| --- | --- | --- | --- | --- |
| Ingredient Name | Concentration | Resistant (R) | Intermediate (I) | Susceptible (S) |
| Ampicillin | 10 µg | ≤13 | 14-16 | ≥17 |
| Ceftazidime | 30 µg | ≤14 | 15-17 | ≥18 |
| Chloramphenicol | 30 µg | ≤12 | 13-17 | ≥18 |
| Ciprofloxacin | 5 µg | ≤15 | 16-20 | ≥21 |
| Clindamycin | 2 µg | ≤14 | 15-20 | ≥21 |
| Erythromycin | 15 ug | ≤13 | 14-22 | ≥23 |
| Gentamycin | 120 µg | ≤6 | 7-9 | ≥10 |
| Imipenem | 10 µg | ≤13 | 14-15 | ≥16 |
| Streptomycin | 10 µg | ≤11 | 12-14 | ≥15 |
| Neomycin | 30 µg | ≤12 | 13-16 | ≥17 |
| Nitrofurantoin | 300 µg | ≤14 | 15-16 | ≥17 |
| Penicillin | 10 U | ≤14 | — | ≥15 |
| Polymyxin B | 300 U | ≤8 | 9-11 | ≥12 |
| Tetracycline | 30 µg | ≤14 | 15-18 | ≥19 |
| Trimethoprim | 5 µg | ≤10 | 11-15 | ≥16 |
| Vancomycin | 30 µg | ≤14 | 15-16 | ≥17 |

The results of antibiotic resistance evaluation of the APsulloc 331261, the APsulloc 331263, the APsulloc 331266 and the APsulloc 331269, compared with *Lactobacillus plantarum* strain (KCTC3108) as a standard strain, are as follows. Table 11: APsulloc 331261 and APsulloc 331263, and Table 12: APsulloc 331266 and APsulloc 331269.

TABLE 11

| | KCTC3108 | | APsulloc 331261 | | APsulloc 331263 | |
| --- | --- | --- | --- | --- | --- | --- |
| Antibiotics | Zone (mm) | Result | Zone (mm) | Result | Zone (mm) | Result |
| Ampicillin | 29 | S | 27 | S | 31 | S |
| Ceftazidime | 23 | S | 16 | I | 15 | I |
| Chloramphenicol | 24 | S | 24 | S | 25 | S |
| Ciprofloxacin | — | R | — | R | — | R |
| Clindamycin | 12 | R | 29 | S | 8 | R |

TABLE 11-continued

| | KCTC3108 | | APsulloc 331261 | | APsulloc 331263 | |
| --- | --- | --- | --- | --- | --- | --- |
| Antibiotics | Zone (mm) | Result | Zone (mm) | Result | Zone (mm) | Result |
| Erythromycin | 26 | S | 25 | S | 27 | S |
| Gentamycin | 20 | S | 19 | S | 19 | S |
| Imipenem | 39 | S | 39 | S | 42 | S |
| Streptomycin | — | R | — | R | — | R |
| Neomycin | 11 | R | 9 | R | 9 | R |
| Nitrofurantoin | — | R | 27 | S | 29 | S |
| Penicillin | 24 | S | 18 | S | 19 | S |
| Polymyxin B | — | R | — | R | — | R |
| Tetracycline | 17 | I | 17 | I | 17 | I |
| Trimethoprim | — | R | — | R | — | R |
| Vancomycin | — | R | — | R | — | R |

TABLE 12

| | KCTC3108 | | APsulloc 331266 | | APsulloc 331269 | |
| --- | --- | --- | --- | --- | --- | --- |
| Antibiotics | Zone (mm) | Result | Zone (mm) | Result | Zone (mm) | Result |
| Ampicillin | 29 | S | 21 | S | 21 | S |
| Ceftazidime | 23 | S | 10 | R | 10 | I |
| Chloramphenicol | 24 | S | 22 | S | 22 | S |
| Ciprofloxacin | — | R | — | R | — | R |
| Clindamycin | 12 | R | 9 | R | 9 | S |
| Erythromycin | 26 | S | 28 | S | 28 | S |
| Gentamycin | 20 | S | 18 | S | 18 | S |
| Imipenem | 39 | S | 39 | S | 39 | S |
| Streptomycin | — | R | — | R | — | R |
| Neomycin | 11 | R | 9 | R | 9 | R |
| Nitrofurantoin | — | R | 27 | S | 27 | S |
| Penicillin | 24 | S | 12 | R | 12 | R |
| Polymyxin B | — | R | — | R | — | R |
| Tetracycline | 17 | I | 17 | I | 17 | I |
| Trimethoprim | — | R | — | R | — | R |
| Vancomycin | — | R | — | R | — | R |

R: Resistant,
I: Intermediate,
S: Susceptible

As can be seen from the above, compared with the standard strain (KCTC3108), the APsulloc 331261 is different in antibiotic resistance pattern of ceftazidime, clindamycin and nitrofurantoin, and the APsulloc 331263 is different in antibiotic resistance pattern of ceftazidime and nitrofurantoin. Compared with the standard strain (KCTC3108), the APsulloc 331266 is different in antibiotic resistance pattern of ceftazidime, nitrofurantoin and penicillin, and the APsulloc 331269 is different in antibiotic resistance pattern of ceftazidime, clindamycin, nitrofurantoin and penicillin. Accordingly, it is confirmed that all of the APsulloc 331261, the APsulloc 331263, the APsulloc 331266 and the APsulloc 331269 are different strains from the standard strain.

When analyzing sugar fermentation pattern, enzyme activity pattern and antibiotic resistance pattern overall, it is confirmed that all of the APsulloc 331261, the APsulloc 331263, the APsulloc 331266 and the APsulloc 331269 are belong to the *Lactobacillus plantarum*, and are different strains from the *Lactobacillus plantarum* standard strain (KCTC3108).

[Test Example 1] Acid Resistance Evaluation (1) Acid Resistance Evaluation Depending on pH The APsulloc 331261 strain culture solution is inoculated to MRS broth 10 mL to the concentration of 0.5%, and cultured at 37° C. overnight. pH is controlled to 2.0, 2.5, 3.0, 3.5, respectively, with HCl. The culture solution 50 μl is inoculated to sterilized MRS broth 5 mL, and then cultured at 37° C. for 1 hour. After 1 hour, the culture solution is diluted with peptone saline buffer solution to measure the number of bacteria per mL. After measuring the number of bacteria in the culture solution, viability is calculated by considering the value multiplying the number by 0.01 as control, and considering the number of control bacteria as 100%.

The method described above is repeated to the APsulloc 331263, the APsulloc 331266 and the APsulloc 331269 strain culture solutions to evaluate acid resistance depending on pH.

The results of comparing acid resistance of the APsulloc 331261, the APsulloc 331263, the APsulloc 331266 and the APsulloc 331269 with the *Lactobacillus plantarum* strain (KCTC3108) as a standard strain are shown in the following Tables. Table 13: APsulloc 331261 and APsulloc 331263, and Table 14: APsulloc 331266 and APsulloc 331269.

TABLE 13

| | KCTC3108 | | APsulloc 331261 | | APsulloc 331263 | |
|---|---|---|---|---|---|---|
| pH | cfu/ml | Viability (%) | cfu/ml | Viability (%) | cfu/ml | Viability (%) |
| Control | $2.9 \times 10^7$ | 100 | $3.8 \times 10^7$ | 100 | $1.9 \times 10^7$ | 100 |
| 2.0 | $3.0 \times 10^1$ | 0 | $1.0 \times 10^1$ | 0 | $<10^1$ | 0 |
| 2.5 | $2.5 \times 10^7$ | 87.4 | $3.3 \times 10^7$ | 87.7 | $1.4 \times 10^7$ | 76.6 |
| 3.0 | $3.2 \times 10^7$ | 110.3 | $3.7 \times 10^7$ | 110.3 | $1.8 \times 10^7$ | 94.7 |
| 3.5 | $2.8 \times 10^7$ | 97.7 | $4.0 \times 10^7$ | 105.3 | $1.8 \times 10^7$ | 93.4 |

TABLE 14

| | KCTC3108 | | APsulloc 331266 | | APsulloc 331269 | |
|---|---|---|---|---|---|---|
| pH | cfu/ml | Viability (%) | cfu/ml | Viability (%) | cfu/ml | Viability (%) |
| Control | $2.9 \times 10^7$ | 100 | $5.0 \times 10^7$ | 100 | $5.0 \times 10^7$ | 100 |
| 2.0 | $3.0 \times 10^1$ | 0 | $<10^1$ | 0 | $3.6 \times 10^2$ | 0 |
| 2.5 | $2.5 \times 10^7$ | 87.4 | $6.0 \times 10^7$ | 118.2 | $5.6 \times 10^7$ | 130.7 |
| 3.0 | $3.2 \times 10^7$ | 110.3 | — | — | $6.5 \times 10^7$ | 112.7 |
| 3.5 | $2.8 \times 10^7$ | 97.7 | $5.8 \times 10^7$ | 114.2 | $6.2 \times 10^7$ | 124.0 |

As can be seen from the above, all of the APsulloc 331261, the APsulloc 331263, the APsulloc 331266 and the APsulloc 331269 show higher viability at about pH 2.5 to 3.5 than the standard strain. Namely, it is confirmed that the above *Lactobacillus plantarum* strains have excellent acid resistance. When considering pH of the stomach with foods is about 2 to 3, it is confirmed that the *Lactobacillus plantarum* strains may have higher viability in the stomach when contained in the food composition.

(2) Acid Resistance Evaluation Depending on Time

The APsulloc 331261 culture solution is inoculated to MRS broth 10 mL to the concentration of 0.5%, and cultured at 37° C. overnight. The culture solution 50 μl, which is controlled to pH 2.5 with HCl, is inoculated to sterilized MRS broth 5 mL, and cultured at 37° C. for 3 hours. After each 1 hour and 3 hours, the culture solution is diluted with peptone saline buffer solution, and then the number of bacteria per mL is measured. After measuring the number of bacteria in the culture solution, viability is calculated by considering the value multiplying the number by 0.01 as control, and considering the number of control bacteria as 100%.

The method described above is repeated to the APsulloc 331263, the APsulloc 331266 and the APsulloc 331269 strain culture solutions to evaluate acid resistance depending on time.

The results of comparing acid resistance of the APsulloc 331261, the APsulloc 331263, the APsulloc 331266 and the APsulloc 331269 with the *Lactobacillus plantarum* strain (KCTC3108) as a standard strain are shown in the following Tables. Table 15: APsulloc 331261 and APsulloc 331263, and Table 16: APsulloc 331266 and APsulloc 331269.

TABLE 15

| | KCTC3108 | | APsulloc 331261 | | APsulloc 331263 | |
|---|---|---|---|---|---|---|
| Time (hr) | cfu/ml | Viability (%) | cfu/ml | Viability (%) | cfu/ml | Viability (%) |
| 0 | $3.3 \times 10^7$ | 100 | $6.8 \times 10^7$ | 100 | $3.4 \times 10^7$ | 100 |
| 1 | $2.9 \times 10^7$ | 86.9 | $6.6 \times 10^7$ | 98 | $2.9 \times 10^7$ | 87.2 |
| 3 | $2.2 \times 10^7$ | 67.3 | $6.4 \times 10^7$ | 94.6 | $2.7 \times 10^7$ | 79.9 |

TABLE 16

| | KCTC3108 | | APsulloc 331266 | | APsulloc 331269 | |
|---|---|---|---|---|---|---|
| Time (hr) | cfu/ml | Viability (%) | cfu/ml | Viability (%) | cfu/ml | Viability (%) |
| 0 | $3.3 \times 10^7$ | 100 | $6.2 \times 10^7$ | 100 | $7.1 \times 10^7$ | 100 |
| 1 | $2.9 \times 10^7$ | 86.9 | $5.7 \times 10^7$ | 91.4 | $7.6 \times 10^7$ | 107.1 |
| 3 | $2.2 \times 10^7$ | 67.3 | $5.8 \times 10^7$ | 92.5 | $5.6 \times 10^7$ | 78.8 |

A can be seen from the above, it is confirmed that all of the APsulloc 331261, the APsulloc 331263, the APsulloc 331266 and the APsulloc 331269 have higher viability at pH 2.5 even after 1 hour and 3 hours, respectively, than the standard strain. Namely, it is confirmed that all of the above *Lactobacillus plantarum* strains have excellent acid resistance for a long time. When considering average retention time of the intaken foods in the stomach is about 1 to 3 hours, it is confirmed that the *Lactobacillus plantarum* strains may have higher viability during the time stayed in the stomach when contained in the food composition.

Thus, all of the APsulloc 331261, the APsulloc 331263, the APsulloc 331266 and the APsulloc 331269 are viable even at lower pH of the stomach during the time stayed in the stomach. Accordingly, when the strains are intaken as a food, those are viable in the stomach, and further, have high intestinal deliverity.

[Test Example 2] Bile Acid Resistance Evaluation

The APsulloc 331261 culture solution is inoculated to MRS broth 10 mL to the concentration of 0.5%, and cultured at 37° C. overnight. Ox gall is added thereto to the concentration of 0.3% and 0.5%, respectively, to prepare a MRS agar plate. MRS agar where the ox gall is not added is used as control. After diluting the strain culture solution and streaking on MRS agar medium, the plate is cultured at 37° C. for 2 days. The results of calculating the number of each colony and the viability (%) of the APsulloc 331261 when considering the number of control bacteria as 100% are shown in the following Tables. The method described above is repeated to the APsulloc 331263, the APsulloc 331266 and the APsulloc 331269 strain culture solutions to evaluate bile acid resistance, and then the results thereof are shown in the following Tables. Table 17: APsulloc 331261 and APsulloc 331266, and Table 18: APsulloc 331263 and APsulloc 331269.

TABLE 17

| Ox Gall Concentration (%) | APsulloc 331261 | | APsulloc 331266 | |
|---|---|---|---|---|
| | cfu/ml | Viability (%) | cfu/ml | Viability (%) |
| 0 | $3.3 \times 10^9$ | 100 | $3.3 \times 10^9$ | 100 |
| 0.3 | $3.2 \times 10^9$ | 96.5 | $3.2 \times 10^9$ | 96.8 |
| 0.5 | $3.0 \times 10^9$ | 89 | $3.0 \times 10^9$ | 85 |

TABLE 18

| Ox Gall Concentration (%) | KCTC3108 | | APsulloc 331263 | | APsulloc 331269 | |
|---|---|---|---|---|---|---|
| | cfu/ml | Viability (%) | cfu/ml | Viability (%) | cfu/ml | Viability (%) |
| 0 | $3.3 \times 10^9$ | 100 | $3.3 \times 10^9$ | 100 | $3.3 \times 10^9$ | 100 |
| 0.3 | $3.2 \times 10^9$ | 97 | $3.2 \times 10^9$ | 111.9 | $3.2 \times 10^9$ | 98.1 |
| 0.5 | $3.0 \times 10^9$ | 91.9 | $3.0 \times 10^9$ | 106.9 | $3.0 \times 10^9$ | 95.3 |

As can be seen from the above, all of the APsulloc 331261, the APsulloc 331263, the APsulloc 331266 and the APsulloc 331269 show excellent bile acid resistance. It is known that the strain having excellent bile acid resistance is also excellent in intestinal fix. Accordingly, it is confirmed that all of the APsulloc 331261, the APsulloc 331263, the APsulloc 331266 and the APsulloc 331269 have excellent intestinal fix and intestinal deliverity.

[Test Example 3] Lactic Acid Producing Ability Evaluation

The APsulloc 331261 strain culture solution is inoculated to MRS broth 10 mL to the concentration of 0.5% and cultured at 37° C. overnight. The culture solution is centrifuged at 8,000 rpm for 15 min, only supernatant is collected. The collected supernatant is treated at 80° C. for 15 min to stop enzyme reaction. The heat treated supernatant is diluted 100 times with distilled water. Later process is conducted by using D-lactic acid/L-lactic acid UV method kit (R-biopharm) according to a manufacturer's protocol. Specific process is as follows Kit solution 1 (glycylglycine buffer/L-glutamate) 1 mL, solution 2 (NAD solution) 0.2 mL and GPT suspension solution 3 0.02 mL are sequentially added to a cuvette. The supernatant prepared above 0.1 mL is added to the cuvette. Deionized water 1 mL is added to control, and deionized water 0.9 mL is added to the sample followed by well mixing thereof. After 5 min, absorbance (A1) is measured at 340 nm. D-LDH solution 4 0.02 mL is added thereto, and mixed well followed by reacting for 30 min. Absorbance (A2) is measured at 340 nm. L-LDH solution 5 0.02 mL is added thereto, and mixed well followed by reacting for 30 min. Absorbance (A3) is measured at 340 nm. The concentrations of D-lactic acid and L-lactic acid in samples are calculated according to a calculating method. The results compared with the *Lactobacillus plantarum* strain (KCTC3108) as a standard strain are shown in the following Table.

The method described above is repeated to the APsulloc 331263, the APsulloc 331266 and the APsulloc 331269 strain culture solutions to evaluate lactic acid producing ability, and the results thereof are shown in the following Tables. Table 19: APsulloc 331261 and APsulloc 331263, and Table 20: APsulloc 331266 and APsulloc 331269.

TABLE 19

| Lactic acid | KCTC3108 | | APsulloc 331261 | | APsulloc 331263 | |
|---|---|---|---|---|---|---|
| | Conc. (g/L) | Ratio (%) | Conc. (g/L) | Ratio (%) | Conc. (g/L) | Ratio (%) |
| D-type | 11.3 | 72 | 8.9 | 62 | 9.2 | 69 |
| L-type | 4.3 | 28 | 5.5 | 38 | 4.2 | 31 |
| Total | 15.6 | 100 | 14.4 | 100 | 13.4 | 100 |

TABLE 20

| Lactic acid | KCTC3108 | | APsulloc 331266 | | APsulloc 331269 | |
|---|---|---|---|---|---|---|
| | Conc. (g/L) | Ratio (%) | Conc. (g/L) | Ratio (%) | Conc. (g/L) | Ratio (%) |
| D-type | | 72 | 10.2 | 62 | 11.7 | 69 |
| L-type | | 28 | 6.3 | 38 | 5.2 | 31 |
| Total | | 100 | 16.5 | 100 | 16.9 | 100 |

As can be seen from the above, all of the APsulloc 331263, the APsulloc 331266 and the APsulloc 331269 produce D-lactic acid and L-lactic acid. Further, the total lactic acid yields of them are smaller than the standard strain, and the ratio of the D-lactic acid to the produced lactic acid is low. Accordingly, foods containing the *Lactobacillus plantarum* strains may be freely taken to adults or infants, who are susceptible to lactic acid, and when foods are fermented by using the *Lactobacillus plantarum* strains, the foods may have gentler flavor.

[Test Example 4] Antibacterial Activity Evaluation (1) APsulloc 331261

The APsulloc 331261 culture solution is inoculated to MRS broth 10 mL to the concentration of 0.5%, and cultured at 37° C. overnight. Sterilized MRS agar 15 mL is aliquoted to a petri dish to prepare a medium, and then each 1 μl of the APsulloc 331261 culture solution is spotted thereon, and cultured at 37° C. for 24 hours.

On the other hand, *Shigella flexneri* is streaked on Tryptic soy agar, and cultured at 37° C. overnight. Then a colony is inoculated to BHI broth and cultured overnight. BHI soft agar (agar 1%) is sterilized and cooled to about 45 to 50° C., and then *Shigella flexneri* culture solution 1% is inoculated thereto.

The *Shigella flexneri* culture solution 10 mL is overlaid on the APsulloc331261 culture solution and hardened. After culturing at 37° C. for 24 hours, size of a clear zone is measured. The results compared with the *Lactobacillus plantarum* strain (KCTC3108) as a standard strain are shown in the following Table.

TABLE 21

| Test Strain | | Clear Zone Diameter (mm) | |
|---|---|---|---|
| KCTC No. | Strain | KCTC3108 | APsulloc 331261 |
| 2008 | *Shigella flexneri* | 26 | 27 |

As can be seen from the above, it is confirmed that the APsulloc 331261 is more excellent in antibacterial effect against the *Shigella flexneri* than the standard strain.

(2) APsulloc 331266

The APsulloc 331266 culture solution is inoculated to MRS broth 10 mL to the concentration of 0.5%, and cultured at 37° C. overnight.

On the other hand, *Listeria monocytogens* and *Bacillus cereus* are streaked on Tryptic soy agar, respectively, and cultured at 37° C. overnight. Then a colony is inoculated to BHI broth and cultured overnight.

BHI soft agar (agar 1%) is sterilized and cooled to about 45 to 50° C., and then *Listeria monocytogens* and *Bacillus cereus* culture solutions 1% are inoculated thereto, respectively. 15 mL of the resulting solutions are aliquoted to a petri dish, respectively, and cooled about 1 hour to prepare a medium. 5 mL of sterilized MRS soft agar (agar 1%) is overlaid on the medium prepared above and hardened. Each 5 μl of the APsulloc 331266 culture solution is spotted on the hardened medium and dried. After culturing at 37° C. for 24 hours, size of a clear zone is measured. The results compared with the *Lactobacillus plantarum* strain (KCTC3108) as a standard strain are shown in the following Table.

TABLE 22

| Test Strain | | Clear Zone Diameter (mm) | |
|---|---|---|---|
| KCTC no. | strain | KCTC3108 | APsulloc 331266 |
| 3710 | *Listeria monocytogens* | 16.8 | 19.3 |
| 3624 | *Bacillus cereus* | 10.3 | 12.3 |

As can be seen from the above, it is confirmed that the APsulloc 331266 is more excellent in antibacterial effect against the *Listeria monocytogens* and the *Bacillus cereus* than the standard strain.

(3) APsulloc 331269

The APsulloc 331269 culture solution is inoculated to MRS broth 10 mL to the concentration of 0.5%, and cultured at 37° C. overnight. The culture solution is centrifuged at 8000 rpm for 5 min, and only supernatant is collected. The supernatant 10 mL is prepared by sterilizing with a 0.22 μl syringe filter.

On the other hand, *Salmonella typhimurium* and *Staphylococcus aureus* are streaked on Tryptic soy agar, respectively, and cultured at 37° C. overnight. Then a colony is inoculated to BHI broth and cultured overnight.

BHI agar is sterilized, and 20 mL thereof is put into a petri dish and cooled to prepare a medium. *Salmonella typhimurium* and *Staphylococcus aureus* culture solutions are diluted 50 times with sterilized physiological saline solution, respectively, and then streaked evenly on the medium prepared above with a sterilized cotton swab. A sterilized paper disk is put thereon, and the supernatant of the APsulloc 331269 culture solution prepared above 100 μl is dropped on the paper disk. The medium is stored at room temperature for about 3 hours for absorption, and then cultured at 37° C. for 24 hours. Size of a clear zone is measured, and the results compared with the *Lactobacillus plantarum* strain (KCTC3108) as a standard strain are shown in the following Table.

TABLE 23

| Test Strain | | Clear Zone Diameter (mm) | |
|---|---|---|---|
| KCTC No. | Strain | KCTC3108 | APsulloc 331269 |
| 2514 | *Salmonella typhimurium* | 8.8 | 9.3 |
| 1621 | *Staphylococcus aureus* | 10 | 10.8 |

As can be seen from the above, it is confirmed that the APsulloc 331269 is more excellent in antibacterial effect against the *Salmonella typhimurium* and the *Staphylococcus aureus* than the standard strain.

The invention claimed is:

1. A method of treating diarrhea, said method comprising administering an effective dose of *Lactobacillus plantarum* APsulloc 331269 (Accession No. KCCM11182P) strain, an extract thereof, or a culture solution thereof to a subject in need of treatment for diarrhea, wherein the strain has acid resistance at pH 2 to pH 4, wherein the strain has bile resistance at 0.3-0.5% bile concentration,
   wherein the strain does not ferment rhamnose, inulin, xylitol, or L-arabinose,
   wherein the strain produces D-type lactic acid in an amount of 70% or less based on a sum of amounts of the D-type lactic acid and L-type lactic acid produced.

2. The method according to claim 1, wherein the strain, the extract thereof, or the culture solution thereof is administered in a composition, wherein the composition further comprises at least one of a surfactant, excipient, wetting agent, emulsifier, suspending agent, salt or buffer for osmotic pressure control, colorant, flavoring agent, stabilizer, preservative, and preserved agent.

3. The method according to claim 1, wherein the strain is isolated from tea tree (*Camellia sinensis*) leaves.

4. The method according to claim 1, wherein the strain has acid resistance at pH 2 to pH 4 for 0.5 hour to 5 hours.

5. The method of claim 1, wherein the effective dose is 0.1 mg/kg/day to 5000 mg/kg/day.

6. The method of claim 1, wherein administration is oral or parenteral.

\* \* \* \* \*